(12) United States Patent
Baker et al.

(10) Patent No.: US 8,864,697 B1
(45) Date of Patent: Oct. 21, 2014

(54) FOOT PAIN TREATMENT DEVICE AND METHOD OF USE

(71) Applicants: Steven Baker, Tampa, FL (US); Joel Levy, Tampa, FL (US)

(72) Inventors: Steven Baker, Tampa, FL (US); Joel Levy, Tampa, FL (US)

( * ) Notice: Subject to any disclaimer, the term of this patent is extended or adjusted under 35 U.S.C. 154(b) by 112 days.

(21) Appl. No.: 13/676,394

(22) Filed: Nov. 14, 2012

(51) Int. Cl.
*A61F 5/00* (2006.01)
*A61F 5/37* (2006.01)
*A61F 5/01* (2006.01)

(52) U.S. Cl.
CPC .................................. *A61F 5/0113* (2013.01)
USPC ............................................ 602/28; 128/882

(58) Field of Classification Search
USPC ........... 602/5, 23, 27–29; 128/882, 892; 2/22, 2/61; 36/88–89, 91–92, 36 R
See application file for complete search history.

(56) References Cited

U.S. PATENT DOCUMENTS

| | | | | |
|---|---|---|---|---|
| 4,938,222 A | * | 7/1990 | Bier, Jr. | 607/111 |
| 5,486,157 A | * | 1/1996 | DiBenedetto | 602/27 |
| 5,700,237 A | * | 12/1997 | Hess | 602/27 |
| 6,267,742 B1 | * | 7/2001 | Krivosha et al. | 602/28 |
| 2010/0050322 A1 | * | 3/2010 | Zagula | 2/239 |

* cited by examiner

*Primary Examiner* — Ophelia A Hawthorne
(74) *Attorney, Agent, or Firm* — Gulf Coast Intellectual Property Group

(57) ABSTRACT

A foot pain treatment device operable to treat foot pain having a tubular member with an integrated orthotic so as to facilitate treatment without the requirement for a shoe. The foot pain treatment device includes a tubular member having a cavity with a first support member disposed within the cavity. The first support member has a first layer and a second layer wherein the second layer is operable to provide temperature therapy. A second support member is provided and is releasably secured to a user wherein the second support member is configured to maintain an angle of a foot so as to provide stretching thereof. At least two straps are provided that are surroundably mounted to a user in order to secure the second support member.

5 Claims, 3 Drawing Sheets

FOOT PAIN TREATMENT DEVICE AND METHOD OF USE

FIELD OF THE INVENTION

The present invention is related to pain treatment devices, more specifically but not by way of limitation a device and method operable to treat foot pain wherein the device includes integrated elements functioning to increase overall ease of use and patient compliance.

BACKGROUND

Millions of individuals suffer from various types of pain on a daily basis. Conditions such muscular or tendon damage that are inflamed as a result of injury or other reason cause individuals significant pain and can be debilitating. Another source of pain results from damage to the human body's connective tissue, more specifically but not by way of limitation, inflammation of the connective tissue, plantar fascia, is a common condition that can result in significant pain for the individual. As is known in the art, the plantar fascia is the connective tissue on the sole of the foot. Inflammation can be a result of overuse or other cause and the condition can be difficult to treat.

One issue with current treatment devices such as commonly available orthotics is the requirement for the individual to utilize a shoe. Conventional orthotics provide a cushioned support surface that is placed within a shoe so as to provide proper support and positioning required to treat the inflamed plantar fascia. Patient compliance with the required utilization of these conventional devices has shown to be a problem.

Another issue with current treatment devices such as conventional orthotics is their inability to provide temperature therapy. Depending upon the foot condition being treated, it is routine to be prescribed either a cold therapy or heat therapy in the treatment thereof. Conventional orthotics are not manufactured of the required materials to deliver the aforementioned temperature therapies. Additionally, dependent upon the severity of the condition, a topical analgesic may be prescribed in order to alleviate the pain. Conventional orthotics are not structured to provide any delivery of topical analgesics or ointments for pain relief.

Additional conventional treatment devices include splints. Conventional splints are utilized to provide stretching of the plantar fascia in order to alleviate the pain. While conventional splints have been shown to be effective, these existing devices are not structured to provide integration with other treatment device.

Accordingly, there is a need for a foot pain treatment device such as but not limited to plantar fasciitis that facilitates improved patient compliance and includes elements not found within existing technologies.

SUMMARY OF THE INVENTION

It is the object of the present invention to provide a foot pain treatment device that includes a tubular member having an integral orthotic support providing a method of delivering therapy for a damaged foot without the requirement to utilize a shoe therewith.

Another object of the present invention is to provide a foot pain treatment device that includes a splint device that is configured to be releasably secured to the tubular member.

Still another object of the present invention is to provide a foot pain treatment device that utilizes a splint that is lockable in at least two angular positions to provide stretching of the foot and/or calf muscles.

Yet another object of the present invention is to provide a foot pain treatment device wherein the integral orthotic includes three layers.

A further object of the present invention is to provide a foot pain treatment device having a tubular member with an integral orthotic wherein the orthotic is manufactured in a plurality of different lengths.

Yet a further object of the present invention is to provide a foot pain treatment device wherein the integral orthotic is manufactured to have different degrees of flexibility.

An additional object of the present invention is to provide a foot pain treatment device wherein at least one layer of the integral orthotic is manufactured from a material to maintain a temperature that is different than that of its surroundings.

A further object of the present invention is to provide a foot pain treatment device having an integral orthotic wherein at least one layer is configured to provide transdermal application of a medication.

Still a further object of the present invention is to provide a foot pain treatment device that is manufactured in different sizes and is further provided in left and right foot configurations.

Another object of the present invention is to provide a foot pain treatment device that is manufactured so as to facilitate a reduced quantity of steps in utilization thereof in order to increase patient compliance.

A further object of the present invention is to provide a foot pain treatment device wherein the tubular member includes a portion to releasably secure to the splint.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
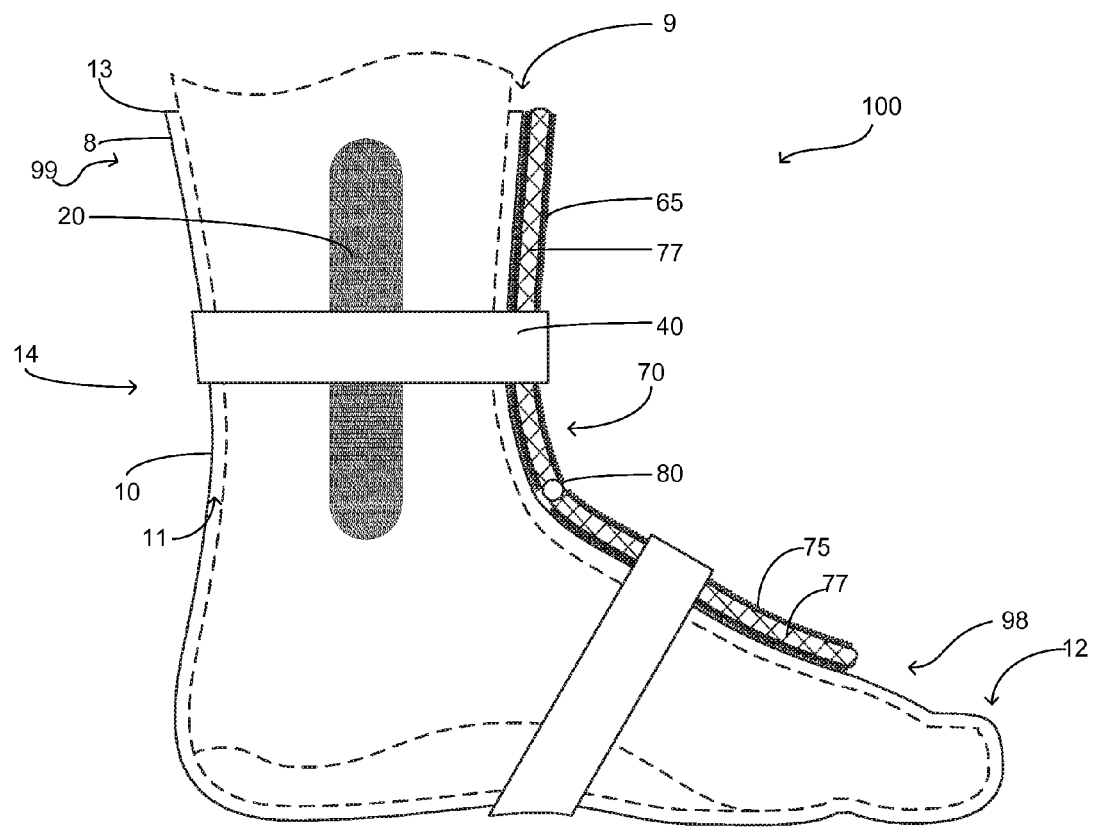
FIG. 1 is a cross-sectional diagrammatic view of the present invention.

Referring now to the drawings submitted herewith, wherein various elements depicted therein are not necessarily drawn to scale and wherein through the views and figures like elements are referenced with identical reference numerals, there is illustrated a foot pain treatment device 100 constructed according to the principles of the present invention.

The foot pain treatment device 100 includes a tubular member 10 having an upper section 99 and lower section 98 that is generally tubular in shape and manufactured from a durable comfortable material such as but not limited to nylon or cotton. The tubular member 10 has a first end 8 having an opening 9 proximate thereto that functions to permit user access to the cavity 11. The tubular member 10 functions similar to a conventional sock wherein a user of the foot pain treatment device 100 inserts a foot through the opening 9 and places the foot such that the toes of the foot are proximate end 12 and the upper perimeter 13 of the tubular member 10 is circumferentially secured around the calf of the user. Secured to the side of the tubular member 10 on the upper section 14 thereof is a fastener 20. The fastener 20 is secured to the upper section 14 of the tubular member 10 utilizing suitable durable techniques such as but not limited to stitching or chemical adhesion. The fastener 20 is generally elongated in shape and is operable to engage the keeper 40 so as to maintain the position of the upper portion 65 of the splint 70 adjacent to the shin area of the user. Additionally, the fastener 20 inhibits the longitudinal movement of the keeper 40 enabling a more stable engagement between the splint 70 and the shin area of a user. The fastener 20 further functions to engage with keeper 40 so as to substantially inhibit the upper section 20 from traversing downward along a user's calf area. While no particular type of fastener 20 is required, good results have been achieved utilizing a fastener 20 manufactured from loop material and a keeper 40 that is manufactured from hook material. It is contemplated within the scope of the present invention that numerous types of fasteners could be utilized in addition to and/or in conjunction with hook and loop material such as but not limited to snaps. Furthermore, while a fastener 20 is illustrated on one side of the tubular member 10 herein, it is contemplated within the scope of the present invention that a fastener 20 could be present on both sides of the tubular member 10. While not illustrated herein, it is contemplated within the scope of the present invention that the tubular member 10 could have disposed on at least a portion of the bottom thereof ant-slip material such as but not limited to rubber. It is further contemplated within the scope of the present invention that the anti-slip material could be provided in numerous different configurations.

Figure 2:
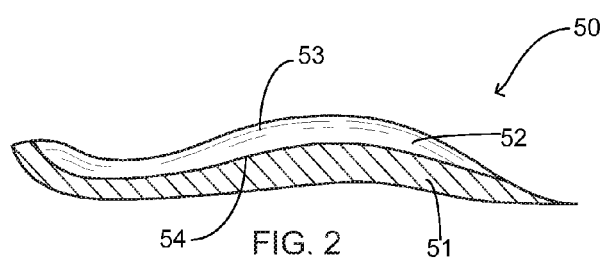
FIG. 2 is a cross-sectional view of the orthotic support of the present invention.

Referring in particular to FIGS. 1 and 2, the foot pain treatment device 100 further includes an orthotic support 50. The orthotic support 50 is integrally secured within the cavity 11 of the tubular member 10 and functions to provide support to at least a portion of the user's foot. The orthotic support 50 is provided in both a left foot and a right foot configuration. The integration of the orthotic support 50 with the tubular member 10 facilitates the utilization of the foot pain treatment device 100 without the need for a shoe or boot. This configuration has been shown to significantly increase patient compliance for prescribed utilization of the foot pain treatment device 100. While no particular length of the orthotic support 50 is required, it is contemplated within the scope of the present invention that the orthotic support 50 is manufactured in approximately three different lengths so as to be suitable for treating most types of foot pain. A first length is contemplated wherein the orthotic support 50 is of sufficient length so as to extend from the posterior edge of the calcaneus to proximal the metatarsal heads. Further, a second length is contemplated for the orthotic support 50 wherein the orthotic support 50 is manufactured to a length extending from the posterior edge of the calcaneus to the sulcus. Lastly, a third length of the orthotic support 50 is contemplated within the scope of the present invention such that the orthotic support 50 extends from the posterior edge of the calcaneus to the distal end of the toes, i.e. the full length of the patients' foot. While the preferred embodiment of the foot pain treatment device 100 has been disclosed to have an orthotic support 50 manufactured having the three aforementioned lengths, it is further contemplated within the scope of the present invention that the orthotic support 50 could be manufactured in numerous different lengths.

As shown in particular in FIG. 2, the orthotic support 50 includes a first layer 51, second layer 52 and third layer 53. The first layer 51 is manufactured from a durable resilient material such as but not limited to plastic or metal. The first layer 51 is generally semi-rigid in structure providing structural support for a foot engaged therewith. The first layer 51 extends substantially the length of the orthotic support 50. The first layer 51 includes an upper surface 54 having an arcuate shaped portion operable to provide support for the arch of a user's foot. It is contemplated within the scope of the present invention that the first layer 51 is manufactured so as to possess a range of flexibility. For example but not by way of limitation, during utilization of the foot pain treatment device 100 it may be desirable to have a first layer 51 that has a stiffness (as measured in pounds per inch) that is configured so as to substantially limit the flexibility thereof and thus of the orthotic support 50 in order to more effectively treat the causes of the foot pain of the user. Alternatively, it is further contemplated within the scope of the present invention that the first layer 51 is manufactured to have a stiffness that is configured with a lower unit of stiffness to allow greater flexibility of the orthotic support 50. Providing the first layer 51 with varying degrees of stiffness increases the effectiveness of the foot pain treatment device 100 during treatment of individual patient needs.

Still referring to FIG. 2, the orthotic support 50 further includes a second layer 52. The second layer 52 is integrally formed with the first layer 51 utilizing suitable durable techniques. The second layer 52 extends substantially the length of the first layer 51 and is manufactured from a gel or similar material functioning to provide pliable support surface at least a portion of the foot of a user. The second layer 52 is further configured to provide thermal treatment for the foot of the user of the foot pain treatment device 100. The second layer 52 is manufactured from a gel material that is operable to maintain a temperature that is different than that of its surroundings. For example but not by way of limitation, a user will place the foot pain treatment device 100 into a freezer or similar appliance in order to reduce the temperature of the second layer 52. Subsequent being place in a freezer or similar appliance, the second layer 52 will maintain a temperature that is cooler than that of its surroundings for a extended period of time so as to provide thermal treatment to the foot of a user of the foot pain treatment device 100. Those skilled in the art will recognize that the second layer 52 could also be operable to maintain a temperature that is greater than that of its surroundings. Utilization of temperature therapy in treating various foot conditions has proven to be effective and the integration of the second layer 52 into the orthotic support 50 enables increased patient compliance and ease of use so as an additional device operable to provide thermal treatment is not required during utilization of the foot pain treatment device 100.

A third layer 53 is included in the orthotic support 50. The third layer 53 is superposed the second layer 52 and is removably secured thereto utilizing suitable durable techniques. The third layer 53 functions to provide transdermal delivery of a topical medication such as but not limited to lidocaine or benzocaine. The third layer 53 consists of a nylon gauze material or other suitable material and is impregnated with a topical anesthetic so as to delivery a dose thereof during utilization of the foot pain treatment device 100. While a particular length of the third layer 53 is illustrated herein, it is contemplated within the scope of the present invention that the third layer 53 could be manufactured in numerous different lengths so as to provide a topical anesthetic to varying portions of a user's foot.

Figure 3:
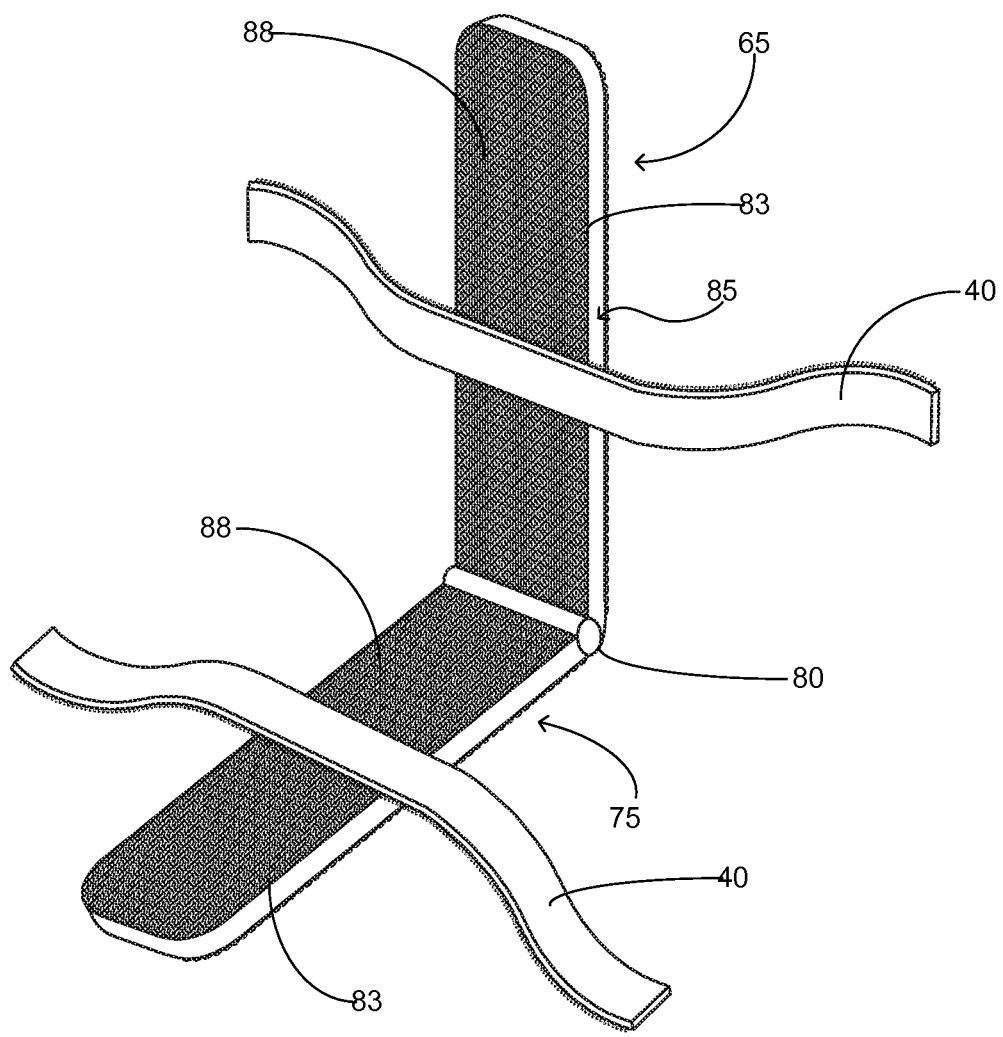
FIG. 3 is a perspective view of the splint of the present invention.

Referring in particular to FIGS. 1 and 3, the splint 70 of the foot pain treatment device 100 is illustrated therein. The splint 70 includes an upper portion 65 and a lower portion 75 that are movably secured via hinge 80. The upper portion 65 and lower portion 75 have an inner layer 77 that are manufactured from a stiff but semi-pliable material such as metal. The splint 70 functions to secure a foot of a user in a desired position such as but not limited to a stretched position in order to provide treatment for a particular condition. The material of the inner layer 77 allows the upper portion 65 and lower portion 75 to be formed against the shin and top of the foot respectively while providing the rigidity required subsequent the splint 70 being placed in a position so as to flex a foot of a user. A hinge 80 is intermediate the upper portion 65 and lower portion 75 and operably couples the upper portion 65 and lower portion 75. The hinge 80 is a rotatable hinge that is lockable in a plurality of different positions so as to facilitate the maintenance of an angular position between the upper portion 65 and lower portion 75. By way of example but not limitation, a user may require temporary flexing of the foot in order to provide treatment for a particular condition. The rotatable and lockable hinge 80 allows the user to position the upper portion 65 and lower portion 75 such that the angle therebetween is less than ninety degrees and lock the position so as to ensure the maintenance of the angle in order to provide effective stretching of the foot. While no particular angle is required between the upper portion 65 and lower portion 75, it is contemplated within the scope of the present invention that the splint is lockable within a range of eighty-five to ninety degrees The upper portion 65 and lower portion 75 further include an outer layer 85 that is surroundably mounted to the inner layer 77. The outer layer 85 is manufactured from a durable soft material such as but not limited to nylon and functions to provide a more comfortable surface for the user. As shown in particular in FIG. 3, the upper portion 65 and lower portion 75 include a top surface 83 that has a fastening mechanism 88 substantially disposed thereon. The fastening mechanism 88 is manufactured from hook and loop material and is designed to be releasably secured to the keeper 40. The fastening mechanism 88 extends substantially the length of the upper portion 65 and lower portion 75 so as to accommodate a keeper 40 in numerous positions therealong or so as to enable the use of more than one keeper 40 on the upper portion 65 and lower portion 75. The keeper 40 is generally elongated in length being manufactured from a durable material having a surface with mateable hook and loop material and is operable to be surroundably mounted to the splint 70 and tubular member 10 so as to secure the splint 70 in a desired position in relation to a foot of a user. The keeper 40 engages the fastening mechanism 88 so as to substantially inhibit the longitudinal movement thereof along the splint 70.

Figure 4:
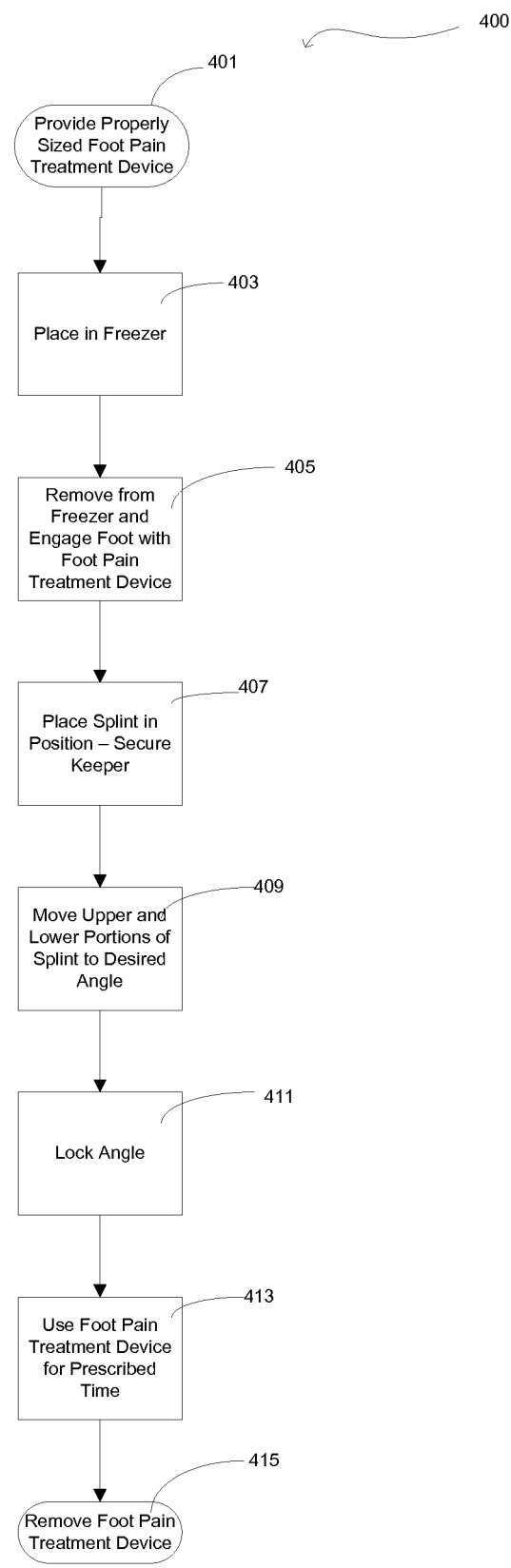
FIG. 4 is a chart diagram of the method of use of the present invention.

Referring in particular to FIG. 4, a flowchart 400 outlining the method of use of the foot pain treatment device 100 is illustrated therein. In step 401, a health practitioner determines the proper size of foot pain treatment device 100 for a patient requiring treatment for foot pain. The proper size of tubular member 10 is selected having an orthotic support 50 integrally formed therein wherein the orthotic support 50 is of a length equivalent to one of the aforementioned three lengths listed herein. The length of orthotic support 50 is determined by the type of pain and/or condition the practitioner is attempting to treat.

Step 403 consists of a user placing the foot pain treatment device 100 in a freezer or similar appliance so as to reduce the temperature of the second layer 52 of the orthotic support 50. As previously discussed herein, the second layer 52 is manufactured from a gel that is operable to maintain a temperature different than that of its surroundings for an extended period of time so as to provide temperature therapy to the foot of a user of the foot pain treatment device 100.

A user will remove the foot pain treatment device 100 from a freezer in Step 405. Subsequent removal of the foot pain treatment device 100, a user will place a foot into the cavity 11 of the tubular member 10 until the phalanges of the user are proximate the second end 12 and at least a portion of the bottom of the foot is superposed the orthotic support 50. As the orthotic support 50 is integrally formed with the tubular member 10, no external shoe or boot is required to retain the placement of the orthotic support 50, which fosters ease of use and significantly increases patient compliance.

In Step 407 and 409, the user will place the splint 70 such that the lower portion 75 is adjacent the top of the foot of a user and the upper portion 65 is adjacent the tibia of a user. Utilizing at least two keepers 40, the user will surroundably mount the keepers 40 around the splint 70 and foot to secure the lower portion 75 while a second keeper 40 will be surroundably mounted the calf area and splint 70 to secure the upper portion 65 in position. In the securing of the upper portion 65, the keeper 40 will be releasably secured to the fastening mechanism 88 as described herein and additionally engage the fastener 20 so as to inhibit the vertical movement of the keeper 40 as well as provide increased stability of the tubular member 10 and upper portion 65 during use of the foot pain treatment device 100. Ensuing the keepers 40 being secured, the user will adjust the angle of the upper portion 65 and lower portion 75 to an angle recommended for treatment of a particular foot ailment. For Steps 407 and 409 it is contemplated within the scope of the present invention that these steps are executed when a user will be either sitting for an extended period of time or lying in bed for an extended period of time. In step 411, the user will utilize the lockable hinge 80 to secure the angle between the upper portion 65 and lower portion 75. The utilization of the lockable hinge 80 provides a technique that ensures the proper angle is maintained during therapy administration. Step 413, a user will wear the foot pain treatment device 100 for the prescribed amount of time as needed to treat the particular foot condition of the user. During the execution of Step 413, the second layer 52 will maintain a temperature that is cooler than that of its environment for at least a portion of the time required to execute Step 413. It is contemplated within the scope of the present invention that the second layer 52 is configured to maintain a temperature that is cooler than that of its surroundings for at least thirty minutes. In Step 415, the foot pain treatment device is removed and stored for subsequent use.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method for relieving foot pain utilizing a foot pain treatment apparatus that does not require a shoe to engage therewith comprising the steps of:

providing a foot pain treatment apparatus that includes a tubular member having an upper portion and a lower portion wherein the lower portion is integrally formed therein, a first support member, said first support member having a first layer and a second layer, wherein said second layer being operable to maintain a temperature different than that of its environment, said tubular member operable to receive a foot therein;

providing a second support member that includes a first section, a second section and an inner layer, said first section and said second section of said second support member having an upper surface and a lower surface, said second support member operable to be releasably secured adjacent to said tubular member, wherein said inner layer of said second support member is manufactured from a formable metal;

placing said tubular member into a freezer or similar appliance so as to cool said second layer;

removing said tubular member from the freezer or similar appliance;

inserting a foot into said tubular member such that said first support member is adjacent the bottom of the inserted foot;

placing said second support member adjacent to said tubular member such that said first section is adjacent a tibia of a user and the second section is adjacent the top of a foot of a user;

securing said second support member in position utilizing at least two straps;

positioning said first section and said second section of said second support member within a range of relative positions of approximately 85 to 90 degrees;

locking the relative position of said first section and said second section of said second support member, holding the inserted foot in the locked relative position while simultaneously applying temperature therapy to the inserted foot;

removing the foot pain treatment apparatus.

2. The method of relieving foot pain as recited in claim 1, wherein the first support member is at least one of the following lengths with respect to the user's foot: posterior edge of a calcaneus to a meta-tarsal joint length, posterior edge of the calcaneus to immediately posterior a phalangeal joint length and posterior edge of the calcaneus to an anterior edge of the phalanges length.

3. The method of relieving foot pain as recited in claim 2, wherein the first support member further includes a third layer, said third layer being superposed said second layer, said third layer operable to transdermally deliver a topical analgesic.

4. The method of relieving foot pain as recited in claim 3 and further comprising, providing a fastener being secured to said upper portion of said tubular member, said fastener operable to releasably secure to a portion of one of said at least two straps, said fastener operable to maintain the position of said upper portion of said tubular member on a calf of a user of the foot pair treatment apparatus.

5. The method of relieving foot pain as recited in claim 4 and further comprising, providing a fastening mechanism disposed on said upper surface of said first section and said second section, said fastening mechanism operable to releasably attach to said at least two straps.

* * * * *